(12) United States Patent
Osborn, III et al.

(10) Patent No.: US 8,603,513 B2
(45) Date of Patent: Dec. 10, 2013

(54) ARTICLE COMPRISING CALCIUM FOR REDUCING THE PRODUCTION OF TSST-1

(75) Inventors: Thomas Ward Osborn, III, Cincinnati, OH (US); Fancheng Wang, Blue Ash, OH (US); Kimberly Ann Nemeth, Mason, OH (US); Catherine Cornick Davis, Sharonville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 669 days.

(21) Appl. No.: 11/823,667

(22) Filed: Jun. 28, 2007

(65) Prior Publication Data

US 2009/0005445 A1 Jan. 1, 2009

(51) Int. Cl.
*A61F 13/02* (2006.01)
(52) U.S. Cl.
USPC .......................................... 424/431
(58) Field of Classification Search
None
See application file for complete search history.

(56) References Cited

U.S. PATENT DOCUMENTS

| | | | |
|---|---|---|---|
| 3,121,427 A | 2/1964 | Mosier | |
| 3,674,030 A * | 7/1972 | Jones et al. | 604/369 |
| 4,428,747 A * | 1/1984 | Friese et al. | 604/12 |
| 4,769,021 A | 9/1988 | Kass | |
| 4,848,572 A * | 7/1989 | Herrera | 206/440 |
| 5,186,965 A * | 2/1993 | Fox et al. | 426/74 |
| 5,409,903 A * | 4/1995 | Polak et al. | 514/23 |
| 5,641,503 A | 6/1997 | Brown-Skrobot | |
| 5,679,369 A | 10/1997 | Brown-Skrobot | |
| 5,705,182 A | 1/1998 | Brown-Skrobot | |
| 6,018,093 A | 1/2000 | Roe et al. | |
| 6,537,970 B1 * | 3/2003 | Vulpescu et al. | 514/25 |
| 6,821,999 B2 | 11/2004 | Syverson et al. | |
| 7,005,453 B1 | 2/2006 | Barney et al. | |
| 7,056,891 B2 | 6/2006 | Resheski-Wedepohl | |
| 2003/0232884 A1 * | 12/2003 | Fink | 514/547 |
| 2006/0223730 A1 * | 10/2006 | Neuls et al. | 510/156 |

FOREIGN PATENT DOCUMENTS

| | | | |
|---|---|---|---|
| WO | WO86/05388 | * | 9/1986 |
| WO | WO 86/05388 | * | 9/1986 |
| WO | WO 2005/016167 A2 | | 2/2005 |

OTHER PUBLICATIONS

Gerg et al., Compendium of Pharmaceutical Excipients for Vaginal Formulations, Pharmaceutical Technology Drug Delivery, 2001, p. 14-18 and 20-24.*
Calcium Equivalents, http://www-users.med.cornell.edu/~spon/picu/calc/cacalc.htm, accessed Sep. 20, 2012.*
Hanna et al. "The relation between vaginal pH and the microbiological status in vaginitis", British Journal of Obsterics and Gynaecology, 92, 1985, pp. 1267-1271.*
"Glycerol Monolaurate Inhibits the Effects of Gram-Positive Select Agents on Eukaryotic Cells", Mamie L. Peterson et al., Department of Microbiology, University of Minnesota Medical School, Received Oct. 1, 2005, Biochemistry 2006, 45, 2387-2397.
PCT International Search Report dated Oct. 16, 2008.

* cited by examiner

*Primary Examiner* — Daniel Sullivan
*Assistant Examiner* — Melissa Javier
(74) *Attorney, Agent, or Firm* — Andrew J. Hagerty; Megan C. Hymore; Amanda T. Barry

(57) ABSTRACT

Articles comprising one or more calcium salts are provided. The articles can contain one or more calcium salts in an amount effective to reduce the production of TSST-1 by at least about 50% when measured by the Shake Flask Method. In certain embodiments, the one or more calcium salts can be substantially non-lethal to *Staphylococcus aureus* when measured by the Shake Flask Method, and/or to *Lactobacillus crispatus, Lactobacillus gasseri*, and/or *Lactobacillus iners* when measured by the Maximum Tolerated Dose Test.

7 Claims, No Drawings

ARTICLE COMPRISING CALCIUM FOR REDUCING THE PRODUCTION OF TSST-1

FIELD OF THE INVENTION

The present invention relates generally to articles including calcium, more particularly to articles including calcium for use in and around the human vagina.

BACKGROUND OF THE INVENTION

In females between the age of menarche and menopause, the normal vagina provides an ecosystem for a variety of microorganisms that is typically maintained in a relatively delicate balance. Bacteria are the predominate type of microorganisms present in the vagina, and most women harbor about $10^7$ to $10^9$ colony forming units (CFU) per ml of vaginal secretion. The more commonly isolated bacteria include lactic acid bacteria, *Lactobacillus* species, *Corynebacteria* species, *Gardnerella vaginalis, Staphylococcus* species, *Peptococcus* species, aerobic and anaerobic streptococcal species, *Bacteroides* species and *Prevotella* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (Herpes simplex). These latter organisms are generally associated with vaginitis or sexually transmitted diseases, although they may be present in low numbers without causing symptoms.

Physiological, social and idiosyncratic factors can affect the cell density and species of microbes present in the vagina. Physiological factors can include age, day of the menstrual cycle, and pregnancy. Social and idiosyncratic factors can include presence and method of birth control, sexual practices, systemic disease (e.g., diabetes), and medication. Disruption of the vaginal ecosystem, such as, e.g., normal healthy vaginal microflora, can permit opportunistic infections to emerge.

Toxic shock syndrome ("TSS") is characterized by rapid onset of high fever, vomiting, diarrhea and rash followed by a drop in blood pressure and vital organ failure. The causative agent of toxic shock syndrome is thought to be exotoxin-producing cocci, such as, e.g., *Staphylococcus*, e.g., *S. aureus*, and/or *Streptococcus*, e.g., *S. pyogenes*. The exotoxins associated with TSS can include, for example, *Staphylococcus*: Enterotoxin A, Enterotoxin B, Enterotoxin C, and Toxic Shock Syndrome Toxin-1 (TSST-1), and *Streptococcus*: pyrogenic Exotoxin A, Exotoxin B, Exotoxin C. It is believed that TSS is not caused by the presence of the bacteria per se, but rather by the toxic effects of the associated exotoxin.

TSS has been associated with the use of absorbent articles within the vagina. The syndrome has also been observed with surgical dressings and nasal packing. TSS appears to occur with elevated frequency in association with absorbent pads having high levels of absorbency.

Various modifications to the absorbent articles have been proposed to reduce the risk of TSS associated with absorbent articles. Typically, such modifications can adversely affect levels of *S. aureus*, or other bacteria that make up the vaginal microflora, such as, e.g., by employing antimicrobials or bactericidal agents. These effects can upset the healthy balance discussed above. In addition, modifications to the absorbent article may not be compatible with manufacture and/or storage techniques and/or may degrade over time.

Accordingly, it would be desirable to provide an improved article, including an absorbent article suitable for use in and around the mammalian vagina, which reduces or prevents the production of TSST-1.

SUMMARY OF THE INVENTION

Articles comprising one or more calcium salts are provided. The articles can contain one or more calcium salts in an amount effective to reduce the production of TSST-1 by at least about 50% when measured by the Shake Flask Method. In certain embodiments, the one or more calcium salts can be substantially non-lethal to *Staphylococcus aureus* when measured by the Shake Flask Method. In certain embodiments, the one or more calcium salts can be substantially non-lethal to *Lactobacillus crispatus, Lactobacillus gasseri*, and/or *Lactobacillus iners* when measured by the Maximum Tolerated Dose Test.

DETAILED DESCRIPTION OF THE INVENTION

The present invention relates to articles comprising calcium salts or compounds. In certain embodiments, the article can include one or more calcium salts in an amount effective to reduce the production of TSST-1. In addition, or alternatively, the one or more calcium salts can be substantially non-lethal to normal vaginal microflora, such as, e.g., *Staphylococcus* and *Lactobacillus* species. Thus, the calcium salts can reduce the production of TSST-1 while generally not affecting normal vaginal microflora, such as bacteria including, e.g., *Staphylococcus aureus, Lactobacillus crispatus, Lactobacillus gasseri*, and/or *Lactobacillus iners.*

As used herein, the term "article" refers to any article wherein the reduction or prevention of the generation of toxins from Gram positive bacteria would be beneficial. Suitable articles can include, e.g., sanitary napkins, panty liners, adult incontinent undergarments, diapers, medical bandages, absorbent articles intended for medical, dental, surgical and/or nasal use, and/or non-absorbent articles intended for use in the human vagina, such as, e.g., pessaries and female contraceptive devices. In certain embodiments, the article can be an absorbent article and/or a vaginal article.

As used herein, the term "absorbent article" refers to devices that absorb and/or contain a substance, such as, e.g., body exudates. A typical absorbent article can be placed against or in proximity to the body of the wearer to absorb and contain various body exudates. Absorbent articles can include, e.g., tampons, surgical wound dressings, sponges, and nasal packings.

As used herein, the term "vaginal article" includes articles intended to be worn in or near the vagina, such as, e.g., disposable absorbent articles that can be worn by women for menstrual and/or light incontinence control, such as, for example, sanitary napkins, tampons, interlabial products, incontinence articles, and liners. Non-absorbent products intended to be worn in the vagina such as, e.g., pessaries for the treatment of vaginal prolapse and/or incontinence, cervical caps, contraceptive sponges, menstrual cups, and contraceptive diaphragms are also included.

As used herein, the term "tampon" refers to any type of absorbent structure such as, e.g., an absorbent mass, that can be inserted into the vaginal canal or other body cavity, such as, e.g., for the absorption of fluid therefrom, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of the material into a tampon. Pledgets are sometimes referred to as tampon blanks or softwinds.

As used herein, the term "vaginal canal" refers to the internal genitalia of the human female in the pudendal region of the body. The terms "vaginal canal" or "within the vagina" as used herein are intended to refer to the space located between the introitus of the vagina and the cervix.

As used herein the term "non-lethal" with regard to bacteria means the cell density of the bacteria is not reduced by more than a factor of about 10 CFU/ml (1 log) of test fluid relative to the control test fluid as measured by the Maximum Tolerated Dose Test ("MTDT") for Lactobacillus species and as measured by the Shake Flask Method for S. aureus.

As used herein the term "lethal" with regard to bacteria means the cell density of the bacteria are reduced by at least a factor of about $10^3$ CFU/ml (3 log) of test fluid relative to the control test fluid as measured by the Maximum Tolerated Dose Test for Lactobacillus species and as measured by the Shake Flask Method for S. aureus.

As used herein, the term "stable" means the calcium salt can have TSST-1 reducing capability as measured by the Shake Flask Method when exposed to conditions such as, e.g., during manufacture and/or storage.

As used herein the term "fugitive" means the calcium salt is capable of moving through the fiber matrix of an article, such as an absorbent article, when the article comprises a plurality of fibers.

As used herein, the term "bound" means less than about 10% of the calcium added to the absorbent article is removed by soaking the article over an 8 hour period at 100° F. in three times the syngyna capacity of sterile physiologic saline solution. The syngyna capacity is determined by the syngyna test (U.S. FDA 21 CFR 801.430, Revised as of Apr. 1, 2006). The percent of "bound" calcium is calculated as (calcium present in the article—calcium in solution) divided by calcium present in the article.

As used herein, the term "partially bound" means less than about 50% of the calcium added to the absorbent article is removed by soaking the article over an 8 hour period at 100° F. in three times the syngyna capacity of sterile physiologic saline solution.

As used herein, the term "substantially bound" means less than about 25% of the calcium added to the absorbent article is removed by soaking the article over an 8 hour period at 100° F. in three times the syngyna capacity of sterile physiologic saline solution.

In certain embodiments, an article can include one or more calcium salts in an amount effective to reduce the production of TSST-1. The production of TSST-1 can be reduced by any suitable amount in the Shake Flask Method, such as, e.g., about 50%, about 60%, about 70%, about 80%, about 90%, about 95%, or more. In certain embodiments, the amount of TSST-1 can be measured by the Shake Flask Method, described below.

In addition, or alternatively, the one or more calcium salts can be substantially non-lethal to *Staphylococcus aureus*, such as, e.g., when measured by the Shake Flask Method, and/or can be substantially non-lethal to *Lactobacillus crispatus, Lactobacillus gasseri*, and/or *Lactobacillus iners*, such as, e.g., when measured by the Maximum Tolerated Dose Test. As such, in certain embodiments, *S. aureus, L. crispatus, L. gasseri*, and/or *L. iners* are not reduced by more than a factor of about 10 CFU/ml (1 log) of test fluid relative to the control test fluid as measured by the Maximum Tolerated Dose Test, such as, e.g., a factor of about 9 CFU/ml of test fluid, a factor of about 8 CFU/ml of test fluid, a factor of about 7 CFU/ml of test fluid, a factor of about 6 CFU/ml of test fluid, a factor of about 5 CFU/ml of test fluid, a factor of about 4 CFU/ml of test fluid, a factor of about 3 CFU/ml of test fluid, a factor of about 2 CFU/ml of test fluid, or less.

In certain embodiments, the calcium salt can have a solubility greater than about 0.3 millimoles/L of water at 25° C., such as, e.g., greater than about 1 millimoles/L of water, greater than about 2 millimoles/L of water, greater than about 4 millimoles/L of water, greater than about 6 millimoles/L of water, greater than about 8 millimoles/L of water, greater than about 10 millimoles/L of water at 25° C., or more.

The calcium salt can be compatible with the tampon making and/or storage process. For example, in certain embodiments, the calcium salt can retain its ability to inhibit toxin following the making process and/or when stored in conditions, such as, e.g., high and/or low temperatures, related to the commercial manufacture and sale. In certain embodiments, the calcium salt can retain its ability to inhibit toxin for any suitable time at any suitable temperature, such as, e.g., at about 100 degrees Celsius for about 3 hours, from about −30 degrees Celsius to about 65 degrees Celsius for about 24 hours, from about 0 degrees Celsius to about 50 degrees Celsius, or any other suitable temperature.

In certain embodiments, the calcium salt can resist acquisition of moisture in a humid environment. Articles, such as, e.g., tampons and/or other absorbent articles, can be exposed to conditions where the relative humidity can exceed 80%, such as, e.g., during commercial storage and/or as in the bathroom during a shower. Some salts, such as, e.g., calcium chloride, magnesium chloride, and/or zinc chloride, are deliquescent substances that can have a strong affinity for moisture and can absorb relatively large amount of fluid from the atmosphere. The use of a deliquescent substance in a tampon can result in moisture being drawn into the tampon such that the tampon can expand, causing insertion into the body or expulsion from the applicator to be difficult. In certain embodiments, the calcium salt can absorb less than about 50% of its initial dry weight as determined by drying 3 hours at 100 degrees C. and then exposed to 80% relative humidity (RH) at 23 degrees C. for 22 hours, such as, e.g., less than about 45%, less than about 40%, less than about 35%, less than about 30%, less than about 25%, less than about 20%, less than about 15%, or less of its initial dry weight.

In certain embodiments, the one or more calcium salts can be calcium lactate and/or calcium citrate malate.

The article can be any suitable article where the reduction of TSST-1 toxin is desirable and/or beneficial. Suitable articles include, e.g., sanitary napkins, tampons, panty liners, interlabial products, adult incontinent undergarments, diapers, surgical wound dressings, sponges, nasal packings, other absorbent articles intended for medical, dental, surgical and/or nasal use, and/or non-absorbent articles intended for use in the human vagina, such as, e.g., pessaries for the treatment of vaginal prolapse and/or incontinence, cervical caps, contraceptive sponges, menstrual cups, and contraceptive diaphragms. In certain embodiments, the article can be suitable for use with a mammal, such as, e.g., a human.

In certain embodiments, the article can be a tampon. The tampon can be formed from a pledget that can be constructed from a wide variety of liquid-absorbing materials suitable for use in absorbent articles. Such materials include, for example, rayon (such as GALAXY rayon (a trilobed rayon) or DANUFIL rayon (a round rayon), both available from Kelheim Fibres GmbH of Kelheim, Germany), cotton, folded tissues, woven materials, nonwoven webs, synthetic and/or natural fibers or sheeting, comminuted wood pulp, which is generally referred to as airfelt, foams, or combinations of these materials. Examples of other suitable materials include: creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these. Additionally, superabsorbent materials, such as superabsorbent polymers or absorbent gelling materials can be incorporated into the tampon.

The tampon can include one or more withdrawal cords and/or overwraps. The withdrawal cord and/or overwrap can be any suitable material, such as, for example, rayon, cotton, bicomponent fibers, polyethylene, polypropylene, other suitable natural or synthetic fibers known in the art, and mixtures thereof. In certain embodiments, the tampon can comprise an overwrap material that substantially encloses the compressed tampon. The tampon can also or alternatively include a secondary absorbent member, such as, for example, a mass of secondary absorbent material attached to the withdrawal cord proximate the withdrawal end of the tampon. Suitable secondary absorbent members are described in, e.g., U.S. Pat. No. 6,258,075.

Any suitable amount of calcium salt can be added and/or included in the article. Suitable amounts include, e.g., an amount effective to reduce the production of TSST-1. In certain embodiments, the amount of calcium added to the article can be greater than about 0.009 millimoles, greater than about 0.01 millimoles, greater than about 0.02 millimoles, greater than about 0.04 millimoles, greater than about 0.06 millimoles, greater than about 0.08 millimoles, greater than about 0.1 millimoles, greater than about 0.5 millimoles, greater than about 1 millimoles, greater than about 2 millimoles, greater than about 3 millimoles, greater than about 4 millimoles, greater than about 5 millimoles, greater than about 6 millimoles, greater than about 7 millimoles, greater than about 8 millimoles, greater than about 8 millimoles, greater than about 9 millimoles, greater than about 10 millimoles or more. In certain embodiments, less than substantially all of the calcium salt that is added to the article is available, such as, e.g., when some of the calcium salt is retained within the article during use and/or when less than substantially all of the calcium salt can be recovered from the article after addition.

The calcium salt can be added to an article by any suitable process and/or at any step in the manufacturing process. In certain embodiments, such as, e.g., when adding calcium salt to a tampon, the calcium salt can be added to the absorbent fiber during the process prior to making the pledget, for example, in the fiber washing and drying steps and/or when a fiber finishing agent is added to facilitate fiber processing. Alternatively, or in addition, the salt can be added to the fiber before the pledget is made or after the pledget is made as an aqueous solution or suspension, or in a non-aqueous solution or suspension or even as a powder. For example, calcium can be added to one or more layers of a pledget prior to compression by exposing one or more portions of the pledget to an aqueous solution or suspension containing the calcium. Examples of methods for exposing a tampon pledget to an aqueous solution include, e.g., spraying the aqueous solution on the pledget, dipping the pledget in the aqueous solution and/or washing the pledget with the aqueous solution. Alternatively, or in addition, one or more calcium salts can be incorporated in the tampon after compression, such as, for example by exposing a substantially completed tampon to an aqueous solution containing the calcium and then drying the tampon. Optionally, the calcium can employ one or more pharmaceutically acceptable and compatible carrier materials. Some suitable examples of carrier materials include, e.g., aqueous solutions, gels, foams, lotions, balms, salves, ointments, boluses, suppositories, and/or combinations thereof. In certain embodiments, it is also possible to add the calcium salt as a powder when the pledget or article is manufactured.

The calcium salt can be included in one or more portions of an article. One such example can be a tampon having the calcium salt incorporated into or on the primary absorbent member, the overwrap, the secondary absorbent member and/or the withdrawal means. In certain embodiments, the calcium salts can also be distributed on, within and/or throughout one or more portions of the tampon. The calcium salt can also be incorporated directly into the absorbent fiber or into the fiber comprising the overwrap during manufacturing of the fiber. In certain embodiments, such as, e.g., when using polyethylene fibers, polypropylene fibers, polyethylene terephthalate fibers, conjugate fibers, bicomponent fibers, rayon fibers, and/or any other suitable synthetic fibers, the calcium salt can be added to the melt prior to the formation of the fibers. As the resulting fibers cool, the calcium salt can migrate to the surface of the fiber. In certain embodiments, an amount of calcium salt can be added such that the amount of calcium that migrates to the surface of the fiber is sufficient to reduce TSST-1 production. The concentration of the calcium salt added to the polymer melt can be any suitable concentration, such as, e.g., between about 10% and about 30%, such as, e.g., between about 15% and about 25% of the fiber weight.

While the distribution of the calcium salt on and/or within an article of the present invention, such as a tampon, can vary as needed, in certain embodiments, the calcium contained in the one or more portions of the article can be distributed such that suitable effectiveness for reducing or prohibiting the production of TSST-1 on or within the article can be attained. The calcium included in the one or more portions of an article of the present invention can be fugitive, loosely adhered, bound, partially bound, substantially bound, or any combination thereof and the like.

An article of the present invention can optionally include other beneficial components commonly found in pharmaceutical compositions, such as, for example vitamins, herbs, aloe, moisturizers, botanicals, supplementary antimicrobials, antiparasitic agents, antipruritics, astringents, local anesthetics, or anti-inflammatory agents. In certain embodiments, the calcium can work in conjunction with one or more of the optionally included components in a complementary or synergistic way.

The present invention is further illustrated by the following examples, which should not be construed as limiting in any way.

EXAMPLES

Example 1

This example demonstrates the reduction of the amount of TSST-1 toxin upon the addition of different calcium salts as measured by the Shake Flask Method.

Materials and Methods

In this example, the amount of TSST-1 toxin produced by *S. aureus* was measured using the Shake Flask Method.

The Shake Flask Method was performed in triplicate with appropriate controls. Twentyfive ml of Brain Heart Infusion broth (BHI) (Difco) was dispensed into 250 ml flasks and the flasks were covered. The medium was autoclaved at 121°-124° C. for 15 minutes and allowed to cool to room temperature.

The calcium solution was prepared by dissolving an appropriate amount of calcium salt into 2.5 mM Phosphate Buffered Saline (PBS). Dilutions of calcium solution were prepared using the following calcium solution (ml) to BHI medium (mls) ratios: 1:49, 5:45, 10:40, and 25:25. Each dilution was tested in triplicate. Each dilution was added to a 250 ml Erlenmeyer Flask. The flasks were inoculated with approximately $10^6$ CFU/ml of an 18-24 hour culture of *Staphylococcus aureus* MN 8 then incubated at 37° C. while shaking for 18-20 hours. A corresponding control of PBS and BHI was also tested. The flasks were removed from the shaker and 3-4 ml of fluid was aseptically removed. A standard plate count analysis and Enzyme-Linked ImmunoSorbent Assay (ELISA) were performed using standard techniques. Results for the test solutions were compared to the appropriate control.

Results

As shown in Table 1, the addition of calcium salt results in a reduction in TSST-1 as measured by the Shake Flask Method. Table 1 further demonstrates that the anion associated with the calcium ion affects the amount of calcium needed to substantially reduce the amount of the TSST-1 toxin measured by the Shake Flask Method.

TABLE 1

| Calcium Salt | Ca (mM) Concentration added to shake flask | % TSST-1 Change (ug/ml) vs. control | % TSST-1 Change (ug/ml/mM) vs. control |
|---|---|---|---|
| chloride | 15.1 | 37 | 2.5 |
| stearate | 9.9 | 65 | 6.6 |
| lactate | 8.8 | 49 | 5.6 |
| citrate malate | 6.8 | 89 | 13.1 |

This example demonstrates that, of the calcium salts tested, calcium citrate malate provides the greatest reduction in TSST-1 toxin at the lowest concentration. Calcium chloride, on the other hand, provides the least reduction in TSST-1 toxin even with the highest concentration.

Example 2

This example demonstrates the reduction of the amount of TSST-1 toxin upon the addition of calcium salts as measured by the Shake Flask Method, along with the solubility of the calcium salts tested.

Materials and Methods

Materials and methods were as described in Example 1.

Results

Table 2 illustrates that the solubility of the calcium salt is related to the calcium salt's ability to reduce TSST-1.

TABLE 2

| Calcium Salt | Ca (mM) Concentration added to shake flask | % TSST-1 Change (ug/ml) vs. control | % TSST-1 Change (ug/ml/mM) vs. control | Solubility (mM of Calcium in $H_2O$ at 25° C. |
|---|---|---|---|---|
| chloride | 75.6 | 82 | 1.1 | 7324 |
| stearate | 98.8 | 62 | 0.6 | <0.003 |
| lactate | 53.1 | 89 | 1.7 | 229 |
| citrate malate | 22.6 | 88 | 3.9 | 45.1 |

As shown in Tables 1 and 2, while calcium stearate at low concentration is more effective than calcium chloride (Table 1) in reducing TSST-1, the effectiveness of calcium stearate does not increase with a higher concentration due to limited solubility. As materials suitable for use in tampons require a solubility of at least about 0.3 millimoles of calcium per L of water to achieve adequate calcium levels in the final tampon, this example further demonstrates that the solubility of certain calcium salts that can reduce TSST-1 activity, such as, e.g., calcium stearate, can be too low for effective use in a tampon.

Example 3

This example demonstrates the reduction of the growth of *S. aureus* and reduction in the amount of TSST-1 toxin upon the addition of calcium salts as measured by the Shake Flask Method.

Materials and Methods

Materials and methods were as described in Example 1.

Results

Table 3 illustrates that calcium salts can reduce TSST-1 levels as measured in the Shake Flask Method, but can also markedly reduce the growth of *S. aureus* relative to the control. Table 3 also shows that calcium acetate and calcium ascorbate virtually eliminate the growth of *S. aureus* relative to controls at the measured concentration.

TABLE 3

| Calcium Salt | Ca (mM/ml) Concentration added to shake flask | % TSST-1 Change (ug/ml) vs. control | Change in *S. aureus* CFU/ml vs. control |
|---|---|---|---|
| acetate | 62.8 | ND | >2 log |
| ascorbate | 75.2 | ND | >2 log |
| lactate | 88.5 | 90% | <1 log |
| citrate malate | 22.6 | 88% | <1 log |

As shown in Table 3, certain calcium salts that reduce TSST-1 production can have an undesirable effect on the cell density of *S. aureus*. As such, this example demonstrates that while the addition of certain calcium salts can reduce TSST-1 levels, the addition of such salts can have an undesirable effect on the vaginal flora, such as, e.g., making those salts unsuitable for use in tampons.

Example 4

This example demonstrates that calcium is more effective than magnesium for inhibiting the amount of TSST-1 toxin produced in the Shake Flask Method. This example further illustrates that zinc, copper, and iron salts can be detrimental to levels of *S. aureus*.

Materials and Methods

Materials and methods were as described in Example 1.

Results

Table 4 shows that calcium is more effective than magnesium in reducing TSST-1 as measured by the Shake Flask Method. Table 4 also illustrates that while zinc, copper, and iron salts reduce toxin compared to control, such salts do so because they are surprisingly lethal to the *S. aureus* bacteria when compared to the control.

TABLE 4

| Compound | Cation (mM) Concentration added to shake flask | % TSST-1 Change (ug/ml) vs. control | Change in S. Aureus CFU/ml vs. control |
|---|---|---|---|
| Calcium chloride | 75.6 | 82% | ≤1 log |
| Magnesium chloride | 74.8 | 47% | ≤1 log |
| Zinc chloride | 74.8 | ND | >2 log |
| Copper chloride | 74.8 | ND | >3 log |
| Ferrous chloride | 74.8 | ND | >2 log |

As such, this example demonstrates that calcium is more effective than magnesium in reducing TSST-1. This example further demonstrates that calcium does not negatively impact the growth of S. aureus as does zinc, copper, and/or iron.

Example 5

This example demonstrates that calcium salts have substantially no effect on *Lactobacillus* bacteria as measured by the Maximum Tolerated Dose Test.
Materials and Methods In this example, the change in *Lactobacillus* levels was measured using the Maximum Tolerated Dose Test (MTDT). The MTDT was performed as follows:

Three microorganisms were tested: *Lactobacillus crispatus* (LMG 12005), *Lactobacillus gasseri* (ATCC 9857), and *Lactobacillus iners* (LMG 18916). A macrotube assay using calcium assay solution was performed individually on each of the three test microorganisms.

*L. gasseri* was grown for 48 hours under anaerobic conditions in Anaerobic CDM Genital Tract Secretions Media (Anerobe Systems, catalog number AS-892a). The inoculum was adjusted to approximately $10^8$ CFU/ml by comparison to a McFarland 0.5 standard. The *L. crispatus* and *L. iners* were grown for 48 hours under anaerobic conditions on chocolate agar (Remel) and the inoculum was made in the genital tract secretions media to a turbidity of approximately $10^8$ CFU/ml by comparison to a McFarland 0.5 standard. Plate counts were performed on all test organism inoculum tubes to determine the exact CFU/ml. All organisms were in logarithmic growth phase prior to analysis of the assay solutions.

A series of five assay solutions of calcium salts were made. Each tube in the seven tube assay (6 experimental and 1 control) contained 7 ml of genital tract secretions media and 3 ml of the stock assay solution or solvent. To each tube in the series 0.1 ml of each individual test organism inoculum was added. The assay tubes were incubated at 35° C. under anaerobic conditions. After 48 hours of incubation, a 0.1 ml aliquot of each assay tube solution was diluted in saline (Remel), plated to chocolate agar (Remel), and incubated at 35° C. under anaerobic conditions to determine the number of viable organisms. Plates containing 30-300 organisms were counted.
Results Table 5 shows calcium salts can be effective in reducing the TSST-1 toxin while having no effect on the keystone *Lactobacillus* vaginal species (*L. cripatus, L. gasseri, L. iners*) associated with vaginal health.

TABLE 5

| Calcium Salt | Ca (mM) Concentration added | Change in L. cripatus vs. control | Change in L. gasseri vs. control | Change in L. iners vs. control |
|---|---|---|---|---|
| citrate malate | 13.5 | <1 log | <1 log | <1 log |
| lacate | 53.1 | <1 log | <1 log | <1 log |

As such, this example and Example 3 demonstrate that calcium salts, such as, e.g., calcium citrate malate and calcium lactate, can reduce TSST-1 while being substantially non-lethal to normal vaginal flora, such as, e.g., *lactobacillus*.

Example 6

This example demonstrates the moisture gain of various calcium salts as measured by the Moisture Gain Test.
Materials and Methods In this example, the moisture gain of the calcium salts tested was determined by the Moisture Gain Test.

Between 0.500 to 2.000 g of calcium salt was placed into a 20 ml Traceclean vial. Both the tare weight of the empty jar and the jar with the salt were recorded. The open vial was placed in an oven for 3 hours at 100° C., and then stored in a desiccator overnight. The jar was sealed and weighed. The "dry weight" of the salt was determined as the difference between the empty tare weight of the jar with lid and the weight of the jar and lid with the salt following drying and storage in the desiccator. The sealed jar was placed under test conditions and the lid was immediately removed. At 3.5, 6.5, and 22 hours, the jar was resealed and weighed. The "wet weight" was determined as the difference between the final weight after exposure to 80% RH at 23° C. and the tare weight of the initial jar and lid. The amount of moisture uptake was calculated as the difference between the "wet weight" and the "dry weight."

Results

Table 6 illustrates that calcium chloride is deliquescent absorbing over 100% of its initial dry weight upon exposure to 80% relative humidity (RH) at 23 degrees C. for 22 hours.

TABLE 6

| Moisture Gain by Calcium salts | | | |
|---|---|---|---|
| RH80% Hours | Calcium chloride % gain | Calcium lactate % gain | Calcium citrate malate % gain |
| 3.5 | 20.2 | 11.9 | 14.8 |
| 6.5 | 34.4 | 17.2 | 16.7 |
| 22 | 117.4 | 29.2 | 17.3 |

This example demonstrates that certain salts, such as, e.g., calcium chloride, can have high levels of moisture gain that may not be suitable to a tampon. An acceptable level of moisture gain is less than about 50%, such as, e.g., less than about 40% as measured by the Moisture Gain test.

Example 7

This example demonstrates the amount of calcium that can be added to a tampon.

Materials and Methods

Calcium solution was added to tampons based on tampon absorbency as calculated by the Syngyna Test.

Results

Table 7 illustrates the amount of calcium (millimoles) that can be added to tampons having different absorbency levels.

TABLE 7

| Calcium added to Tampon | | | | | |
|---|---|---|---|---|---|
| | Tampon Absorbency (grams) | | | | |
| | 4 | 9 | 12 | 14 | 18 |
| Ca (mmoles) | 0.009 | 0.020 | 0.027 | 0.034 | 0.041 |

This example demonstrates the amount of calcium that can be added to a tampon based on the article capacity in certain embodiments.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising one or more calcium salts in an amount greater than about 0.009 millimoles of calcium to reduce the production of TSST-1 by at least about 50% when measured by the Shake Flask Method, wherein the one or more calcium salts are calcium lactate and/or calcium citrate malate, wherein the absorbent article is a vaginal article, wherein the one or more calcium salts are incorporated into a polymer selected from the group consisting of polyethylene, polypropylene, polyester, polyurethane, silicones, rayon, and combinations thereof.

2. The absorbent article of claim 1, wherein the absorbent article is a tampon.

3. The absorbent article of claim 1, wherein the absorbent article is a pessary, sanitary napkin, panty liner, or incontinence pad.

4. The absorbent article of claim 1, wherein the amount of calcium salt is sufficient to reduce the production of TSST-1 by at least about 70%.

5. The absorbent article of claim 2, wherein the amount of calcium salt is sufficient to reduce the production of TSST-1 by greater than about 2 μg/ml/mM, and wherein the one or more calcium salts are provided in a concentration greater than about 20 mM.

6. The absorbent article of claim 1 wherein the one or more calcium salts is calcium citrate malate.

7. An article comprising one or more calcium salts in an amount greater than about 0.009 millimoles of calcium to reduce the production of TSST-1 by at least about 50% when measured by the Shake Flask Method; wherein the one or more calcium salts are substantially non-lethal to *Staphylococcus aureus* when measured by the Shake Flask Method; wherein the one or more calcium salts are substantially non-lethal to *Lactobacillus crispatus, Lactobacillus gasseri,* and *Lactobacillus iners* when measured by the Maximum Tolerated Dose Test; wherein the one or more calcium salts have a moisture gain of less than about 50% after 22 hours as determined by the Moisture Gain Test; wherein the one or more calcium salts are selected from the group consisting of calcium lactate, calcium citrate malate, and combinations thereof; and wherein the article is an absorbent vaginal article in the form of a tampon.

* * * * *